(12) United States Patent
Isaacson et al.

(10) Patent No.: US 11,116,419 B2
(45) Date of Patent: Sep. 14, 2021

(54) INVASIVE MEDICAL DEVICES INCLUDING MAGNETIC REGION AND SYSTEMS AND METHODS

(71) Applicant: Becton, Dickinson and Company, Franklin Lakes, NJ (US)

(72) Inventors: S. Ray Isaacson, Layton, UT (US); Siddarth Shevgoor, Sandy, UT (US); Jonathan Karl Burkholz, Salt Lake City, UT (US); Laurie Sanders, Glen Ridge, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 501 days.

(21) Appl. No.: 15/170,497

(22) Filed: Jun. 1, 2016

(65) Prior Publication Data
US 2017/0347913 A1 Dec. 7, 2017

(51) Int. Cl.
*A61B 5/06* (2006.01)
*A61B 17/34* (2006.01)
(Continued)

(52) U.S. Cl.
CPC ............ *A61B 5/062* (2013.01); *A61B 8/0841* (2013.01); *A61B 17/3403* (2013.01); *A61M 25/0082* (2013.01); *A61M 25/0127* (2013.01); *A61B 5/489* (2013.01); *A61B 2017/3413* (2013.01); *A61B 2034/2051* (2016.02); *A61B 2090/3929* (2016.02); *A61B 2090/3954* (2016.02)

(58) Field of Classification Search
CPC ... A61B 5/062; A61B 8/0841; A61B 17/3403; A61B 2034/2051; A61B 2090/3954; A61B 2017/3413; A61M 25/0082; A61M 25/0127; A61M 5/343
USPC .................................................. 600/409, 424
See application file for complete search history.

(56) References Cited

U.S. PATENT DOCUMENTS 4,161,943 A 7/1979 Nogier
5,000,912 A * 3/1991 Bendel ............ A61B 17/06066
148/325

(Continued)

FOREIGN PATENT DOCUMENTS

CN 201138912 Y 10/2008
DE 3742298 A1 6/1989
(Continued)

OTHER PUBLICATIONS

Nave, R. Ferromagnetism [online], Georgia State University, HyperPhysics, Jul. 1, 2006 [retrieved on Oct. 12, 2018], Retrieved from the Internet: <URL: https://web.archive.org/web/20060701023036/http://hyperphysics.phy-astr.gsu.edu/hbase/Solids/ferro.html>. p. 1.*
(Continued)

*Primary Examiner* — Carolyn A Pehlke
*Assistant Examiner* — Victoria Fang
(74) *Attorney, Agent, or Firm* — Servilla Whitney LLC (57) ABSTRACT

Devices, systems, and methods are described including an invasive medical device with a magnetic region. The magnetic region can include a discontinuity in the magnetic region providing a diameter transition, a plurality of spaced magnetic regions can be provided or the magnetic regions can be encoded with data. Systems and methods are described that include ways to read the data.

13 Claims, 10 Drawing Sheets

(51) Int. Cl.
    *A61B 90/00*    (2016.01)
    *A61B 34/20*    (2016.01)
    *A61M 25/01*    (2006.01)
    *A61B 8/08*     (2006.01)
    *A61M 25/00*    (2006.01)
    *A61B 1/00*     (2006.01)
    *A61B 5/00*     (2006.01)

(56) References Cited

U.S. PATENT DOCUMENTS

| | | | |
|---|---|---|---|
| 5,215,528 A | | 6/1993 | Purdy et al. |
| 5,461,311 A * | | 10/1995 | Nakazato ............ F15B 15/2861 |
| | | | 324/207.24 |
| 5,558,651 A | | 9/1996 | Crawford et al. |
| 5,955,881 A | | 9/1999 | White et al. |
| 6,263,230 B1 | | 7/2001 | Haynor et al. |
| 6,432,036 B1 | | 8/2002 | Kim |
| 6,475,226 B1 | | 11/2002 | Belef et al. |
| 7,932,718 B1 * | | 4/2011 | Wiegert ................ G01V 3/081 |
| | | | 324/245 |
| 7,935,080 B2 * | | 5/2011 | Howell ................ A61M 5/3273 |
| | | | 604/110 |
| 9,492,097 B2 | | 11/2016 | Wilkes et al. |
| 2002/0042581 A1 | | 4/2002 | Cervi |
| 2003/0100829 A1 | | 5/2003 | Zhong et al. |
| 2004/0176683 A1 * | | 9/2004 | Whitin .................. A61B 5/068 |
| | | | 600/424 |
| 2005/0165301 A1 * | | 7/2005 | Smith ............... A61M 25/0043 |
| | | | 600/421 |
| 2007/0016131 A1 | | 1/2007 | Munger et al. |
| 2007/0049846 A1 * | | 3/2007 | Bown ............... A61M 25/0127 |
| | | | 600/585 |
| 2007/0249901 A1 * | | 10/2007 | Ohline ................. A61B 5/068 |
| | | | 600/117 |
| 2009/0012517 A1 * | | 1/2009 | de la Rama ........... A61B 34/73 |
| | | | 606/41 |
| 2010/0036238 A1 * | | 2/2010 | Neidert .................. A61B 5/06 |
| | | | 600/424 |
| 2010/0217275 A1 * | | 8/2010 | Carmeli ........... A61B 17/22012 |
| | | | 606/128 |
| 2010/0230862 A1 | | 9/2010 | Arney et al. |
| 2011/0196397 A1 | | 8/2011 | Frantz et al. |
| 2011/0267043 A1 * | | 11/2011 | Dolsak ................ G01D 5/2455 |
| | | | 324/207.11 |
| 2012/0016316 A1 | | 1/2012 | Zhuang et al. |
| 2012/0041297 A1 | | 2/2012 | McGary |
| 2012/0095319 A1 | | 4/2012 | Kondrosky et al. |
| 2012/0143029 A1 | | 6/2012 | Silverstein et al. |
| 2013/0075649 A1 * | | 3/2013 | Wang .................... B82Y 30/00 |
| | | | 252/62.55 |
| 2013/0123704 A1 | | 5/2013 | Bierman et al. |
| 2013/0131547 A1 | | 5/2013 | Hardert et al. |
| 2014/0031674 A1 | | 1/2014 | Newman et al. |
| 2014/0046261 A1 | | 2/2014 | Newman et al. |
| 2014/0107475 A1 | | 4/2014 | Cox et al. |
| 2014/0135595 A1 | | 5/2014 | Powell et al. |
| 2014/0180328 A1 | | 6/2014 | Vaccaro et al. |
| 2014/0241946 A1 * | | 8/2014 | Self ........................ G01N 35/04 |
| | | | 422/65 |
| 2014/0253270 A1 | | 9/2014 | Nicholls et al. |
| 2014/0257080 A1 * | | 9/2014 | Dunbar ................ A61B 8/4416 |
| | | | 600/409 |
| 2015/0080710 A1 * | | 3/2015 | Henkel ................ H01F 13/003 |
| | | | 600/424 |
| 2015/0306319 A1 | | 10/2015 | Nessel et al. |
| 2015/0320977 A1 | | 11/2015 | Vitullo et al. |
| 2015/0359991 A1 | | 12/2015 | Dunbar et al. |
| 2016/0361519 A1 | | 12/2016 | Teoh et al. |

FOREIGN PATENT DOCUMENTS

| | | | | |
|---|---|---|---|---|
| EP | 0320623 | A1 | 11/1988 | |
| JP | H0327774 | A | 2/1991 | |
| JP | H08509141 | A | 10/1996 | |
| JP | 2008512270 | A | 4/2008 | |
| JP | 2009505744 | A | 2/2009 | |
| JP | 2014501143 | A | 1/2014 | |
| JP | 2015518752 | A | 7/2015 | |
| JP | 2016059549 | A | 4/2016 | |
| WO | 2009152486 | A1 | 12/2009 | |
| WO | 2013/034175 | A1 | 3/2013 | |
| WO | 2013142386 | A1 | 9/2013 | |
| WO | 2014052894 | A2 | 4/2014 | |
| WO | 2014062728 | A1 | 4/2014 | |
| WO | WO-2016187456 | A1 * | 11/2016 | ............... A61B 7/00 |

OTHER PUBLICATIONS

Laser Welding in Medical Device Technology [online], Rofin, May 8, 2015 [retrieved on Jan. 26, 2019], Retrieved from the Internet: <URL: https://web.archive.org/web/20150508080208/https://www.rofin.com/en/markets/medical-device-technology/laser-welding/>.*

Ferrite Toroids [online]. Magnetics, Sep. 1, 2010 [retrieved on Oct. 16, 2018], Retrieved from the Internet: <URL: https://web.archive.org/web/20100901184145/https://www.mag-inc.com/Products/Ferrite-Cores/Ferrite-Toroids>.*

Honnegowda, Lakshmisha, et al. Security Enhancement for Magnetic Data Transaction in Electronic Payment and Healthcare Systems [online], IACSIT International Journal of Engineering and Technology, Apr. 2013 [retrieved on Sep. 5, 2019], vol. 5, No. 2. Retrieved from the Internet: [URL/DOI: see Office action].*

PCT International Search Report and Written Opinion in PCT/US2017/033986 dated Aug. 28, 2017, 17 pages.

Non-Final Office Action in U.S. Appl. No. 15/604,244 dated Jun. 27, 2019, 50 pages.

PCT International Preliminary Report on Patentability & Written Opinion in PCT/US2017/034517, dated Dec. 4, 2018, 8 pgs.

PCT International Preliminary Report on Patentability and Written Opionin in PCT/US2017/034515, dated Dec. 4, 2018, 8 pgs.

PCT International Preliminary Report on Patentability & Written Opinion in PCT/US2017/034515, dated Dec. 4, 2018, 8 pgs.

Final Office Action in U.S. Appl. No. 15/604,244 dated Jan. 10, 2020, 63 pages.

Bhattacharya, Deepamala. ALNICO [online], Chemistry Learner, May 31, 2014 [retrieved on Mar. 2, 2020], Retrieved from the Internet: <URL: https://web.archive.org/web/20140531135446/http://www.chemistrylearner.com/alnico.html> (Year: 2014).

Final Office Action in U.S. Appl. No. 15/154,348 dated May 15, 2020, 10 pages.

Non-Final Office Action in U.S. Appl. No. 15/154,353 dated Mar. 17, 2020, 12 pages.

Non-Final Office Action in U.S. Appl. No. 15/170,531 dated Mar. 17, 2020, 38 pages.

Final Office Action in U.S. Appl. No. 15/154,353 dated Jun. 24, 2020, 12 pages.

Non-Final Office Action in U.S. Appl. No. 15/170,531, dated Sep. 18, 2020, 39 pages.

Non-Final Office Action in U.S. Appl. No. 15/604,244, dated Sep. 15, 2020, 97 pages.

Final Office Action in U.S. Appl. No. 15/604,244 dated Mar. 16, 2021, 112 pages.

Final Office Action in U.S. Appl. No. 15/170,531 dated Mar. 3, 2021, 39 pages.

Non-Final Office Action in U.S. Appl. No. 15/170,518 dated Feb. 19, 2021, 21 pages.

Final Office Action in U.S. Appl. No. 15/170,518, dated Jul. 8, 2021, 49 pages.

* cited by examiner

FIG. 14

INVASIVE MEDICAL DEVICES INCLUDING MAGNETIC REGION AND SYSTEMS AND METHODS

FIELD

Principles and embodiments of the present disclosure relate generally to devices including a magnetic region and systems and methods utilizing such devices.

BACKGROUND

Traditionally, penetration of an invasive medical device such as a needle and catheter tubing through skin tissue to reach the vein during catheter insertion is invisible to clinicians. For this reason, they must rely on their first-hand experience with needle insertion in combination with tactile sense to successfully identify the location of the vein. This may be a difficult task when attempting to access a small vein in a deep location under the skin, increasing risk of excess pain and/or injury to the patient. There are similar problems with insertion of other invasive medical devices such as guidewires, catheter introducers and stylets with respect to the inability to precisely visualize the location of the invasive medical device.

Emerging procedural guidance systems utilize a combination of ultrasound and magnetic technologies to provide visualization of subdermal anatomy and device position in the in-plane and out-of-plane orientations. This combination of ultrasound and magnetic methods also allows for the projection or anticipation of the insertion device position relative to the patient's anatomy, and thereby improves the likelihood of successfully accessing the vascular and completing the invasive procedure.

One leading technology targets the a portion of the device that is inserted into the patient, e.g., the needle cannula, as the portion of the invasive device for magnetization, while another leading technology uses a permanent magnet located on the hub (e.g., needle hub) of the device. Although a permanent magnet offers a more reliable magnetic field as it is not subject to the variation of the clinician magnetizing the needle at the point of use, it does rely more on a calculated projection of the needle tip location. The system that relies on magnetizing the cannula prior to insertion can more reliably measure the actual tip location, but this method is subject to variability on consistently magnetizing the cannula as it relies on the clinician to place the needle into a magnetic device to magnetize the needle. Furthermore current needle guidance systems typically utilize a magnetic field generated by magnetizing the needle by burying the needle into the magnetizer until the point of the needle hits a rubber stopping surface. Damage can occur that is not apparent to the user that can negatively affect the insertion process.

In addition, both of these systems utilize a magnetic field generated by a portion of the cannula sub-assembly, and therefore, the system is not able to measure or predict relative motion between the needle hub and catheter adapter sub-assemblies. Understanding the relative position and motion of these two sub-assemblies can be used to inform a clinician of procedurally important states of the insertion process, such as when the needle tip reaches the vein, when the catheter tip reaches the vein, when the catheter is advanced to cover the needle tip ("hooding the catheter") and thereby safe for further advancement.

It would be desirable to provide medical devices, system and methods that could be used with devices, systems and methods to provide improved visualization during penetration of a needle through a patient's skin tissue.

SUMMARY

Various embodiments are listed below. It will be understood that the embodiments listed below may be combined not only as listed below, but in other suitable combinations in accordance with the scope of the disclosure.

A first aspect of the disclosure pertains to an invasive medical device for insertion into a patient, the device comprising an elongate shaft having a diameter, an outer surface, a distal tip, and a proximal end, the diameter of the elongate shaft sized to be inserted within an intravenous catheter, at least a portion of the elongate shaft having a first magnetic region and a discontinuity in the first magnetic region providing a diameter transition such that the shaft includes an increased diameter region.

A second aspect pertains to an invasive medical device for insertion into a patient, the device comprising an elongate shaft having a diameter, an outer surface, a distal tip, and a proximal end, the diameter of the elongate shaft sized to be inserted within an intravenous catheter, at least a portion of the elongate shaft having a first magnetic region having a first magnetic field B1 and length L1 and spaced at a distance d from a second magnetic region having a second magnetic field B2 and second length L2, wherein L1 and L2 are not equal.

A third aspect pertains to an invasive medical device for insertion into a patient, the device comprising an elongate shaft having a diameter, an outer surface, a distal tip, and a proximal end, the diameter of the elongate shaft sized to be inserted within an intravenous catheter, at least a portion of the elongate shaft having a first magnetic region having a first magnetic field B1 and a first length L1 and spaced at a distance d from a second magnetic region having a second magnetic field B2 and a second length L2, wherein the first magnetic region is adjacent the distal tip. In one embodiment of the third aspect the device has at least a third magnetic region spaced proximally from the second magnetic region, the third magnetic region having a third magnetic field B3 and length L3. In an embodiment, of the third aspect, the first magnetic region and the second magnetic region are encoded with data. In an embodiment of the third aspect, the data includes information about the invasive medical device, the information including one or more of diameter, length and type of device.

A fourth aspect pertains to a system for determining relative position of a needle comprising the invasive medical device described herein and magnetometers positioned with respect to the first magnetic region, and the second magnetic region. A fifth aspect pertains to a method obtaining information about an invasive medical device having a distal tip, the method comprising encoding magnetic data on an invasive medical device with a plurality of magnetic fields, the medical device selected a guidewire, a catheter introducer, a stylet and a hypodermic needle; and reading the data encoded on the invasive medical device.

DETAILED DESCRIPTION

Before describing several exemplary embodiments, it is to be understood that the disclosure is not limited to the details of construction or process steps set forth in the following description. The disclosure is capable of other embodiments and of being practiced or being carried out in various ways.

Reference throughout this specification to "one embodiment," "certain embodiments," "various embodiments," "one or more embodiments" or "an embodiment" means that a particular feature, structure, material, or characteristic described in connection with the embodiment is included in at least one embodiment. Thus, the appearances of the phrases such as "in one or more embodiments," "in certain embodiments," "in various embodiments," "in one embodiment" or "in an embodiment" in various places throughout this specification are not necessarily referring to the same embodiment. Furthermore, the particular features, structures, materials, or characteristics may be combined in any suitable manner in one or more embodiments.

Reference will now be made to figures wherein like structures will be provided with like reference designations. It is understood that the drawings are diagrammatic and schematic representations of exemplary embodiments, and are neither limiting nor necessarily drawn to scale. The present disclosure relates to medical devices, systems and methods for enhancing visualization of an invasive procedure requiring procedural guidance, such as providing enhanced visualization of a vascular access device during an invasive insertion procedure. In one embodiment, a magnetic feature is placed on the invasive medical device, for example, on a needle, which allows the magnetic feature to be placed closer to the tip, thus increasing the precision of the placement guidance. Embodiments of the disclosure pertain to an invasive medical device with a shaft, a least a portion of which have a magnetic region. The magnetic region can be provided in a variety of ways, including a layer ferromagnetic metal, a layer of paramagnetic metal, a spot weld of magnetic metal, a ferrule and combinations thereof. In other embodiments, the magnetic region can be provided by changing the composition of the region to increase the magnetic susceptibility of the region, or the magnetic region can be provided by cold working the invasive medical device. In specific embodiments, there is a discontinuity in the magnetic region. In other embodiments, the shaft has at least two magnetic regions. In one or more embodiments, the magnetic regions are encoded with data. The medical devices described herein can be used in various systems and methods described further below.

In one or more embodiments, the invasive medical devices are part of a catheter adapter including a needle subassembly that can be used and a catheter adapter subassembly. In an embodiment the catheter adapter subassembly includes either a permanent magnet element or magnetizable feature.

It is to be understood that the word "proximal" refers to a direction relatively closer to a clinician using the device to be described herein, while the word "distal" refers to a direction relatively further from the clinician. For example, the end of a needle placed within the body of a patient is considered a distal end of the needle, while the needle end remaining outside the body is a proximal end of the needle. "Magnetic feature" refers to a feature that includes a permanent magnet and/or a magnetizable material that has been magnetized by an externally applied magnetic field such that the magnetic feature can be detected by an ultrasound system. A "magnetizable feature" refers to an element that can become magnetized and is detectable by an ultrasound system as described further herein. "Invasive medical device" refers to devices that are inserted into the vasculature of a patient such as a needle, a catheter introducer and a stylet. In specific embodiments, "invasive medical device" refers to a medical device that is sized and shaped to be inserted into an intravenous catheter.

Figure 1:
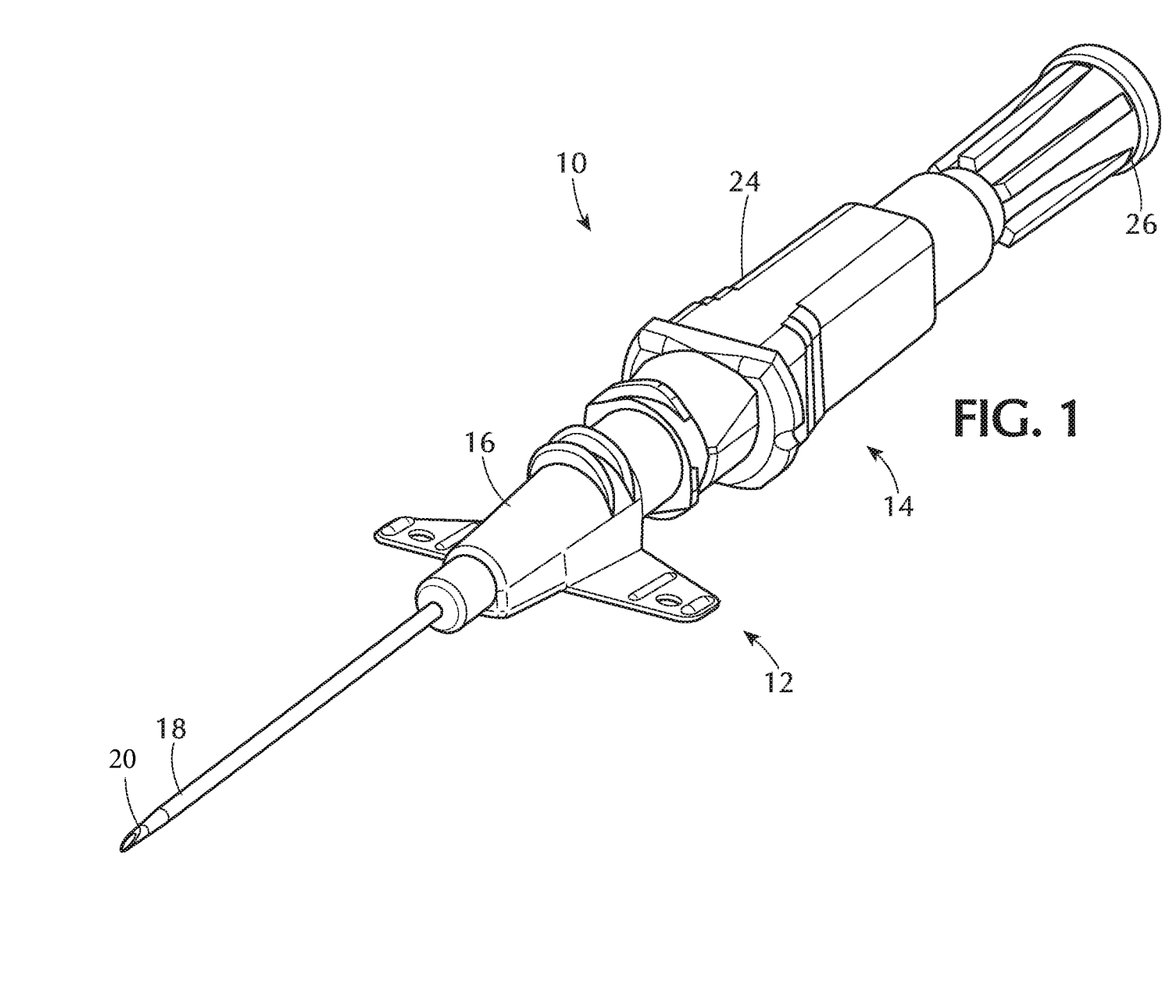
FIG. 1 is a perspective view of a catheter assembly that can be utilized according to an embodiment.
Figure 2:
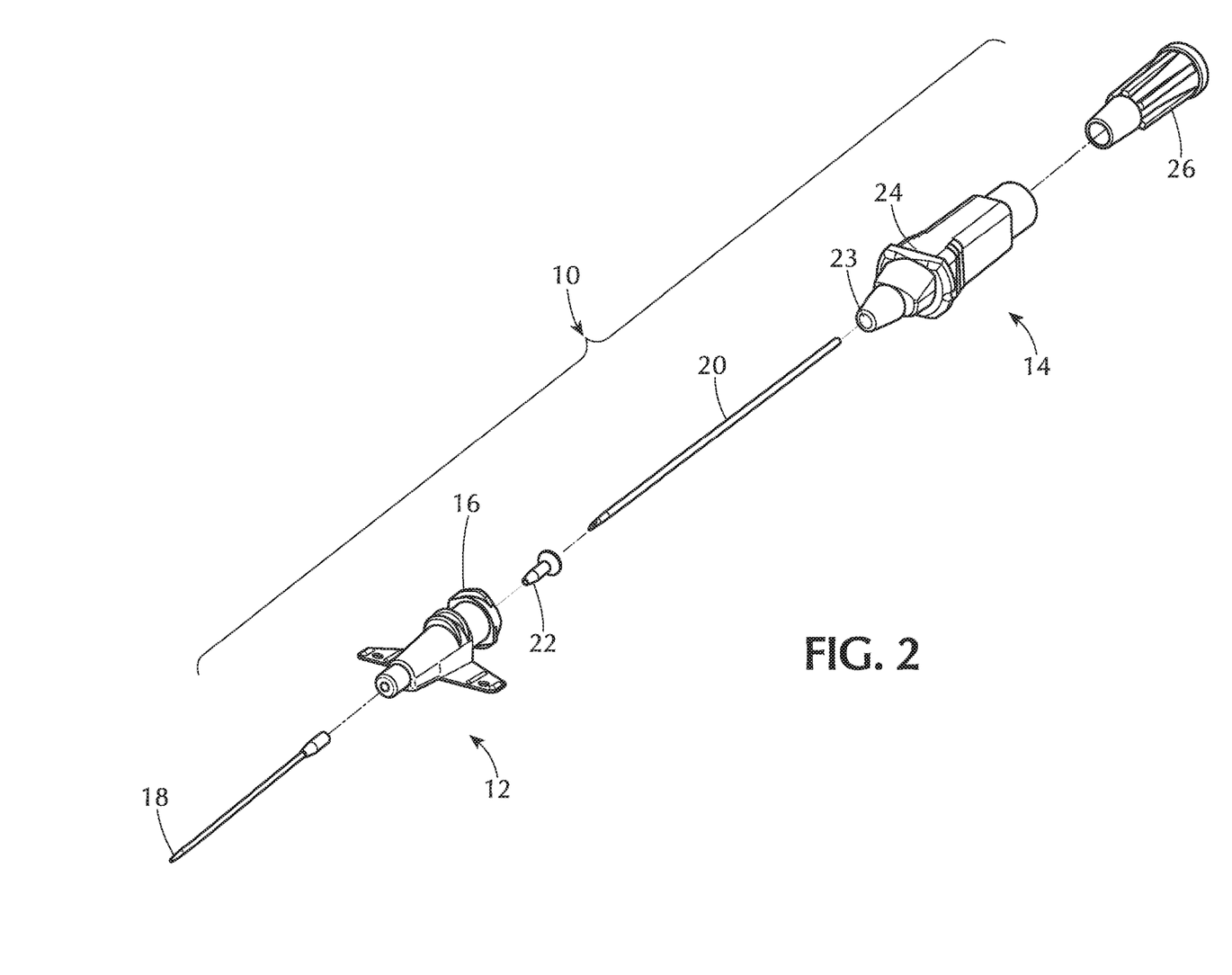
FIG. 2 is an exploded perspective view of the catheter assembly shown in FIG. 1.
Figure 3:
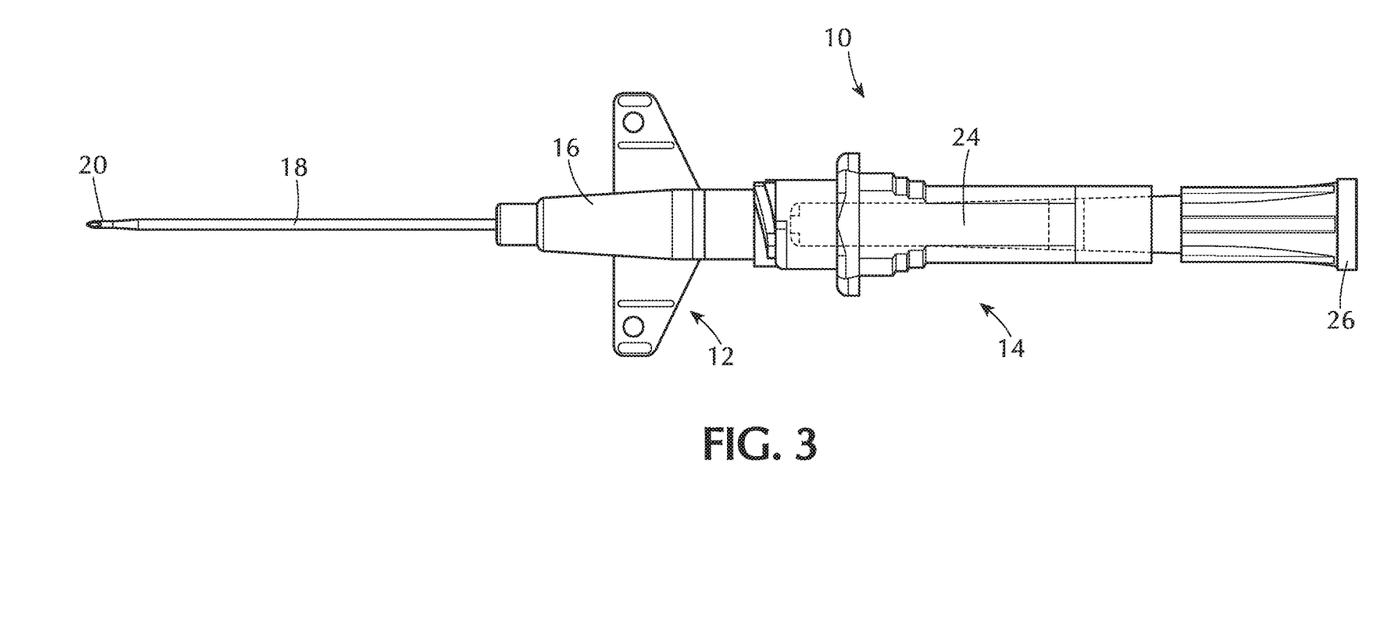
FIG. 3 is a top plan view of the catheter assembly shown in FIG. 1.
Figure 4:
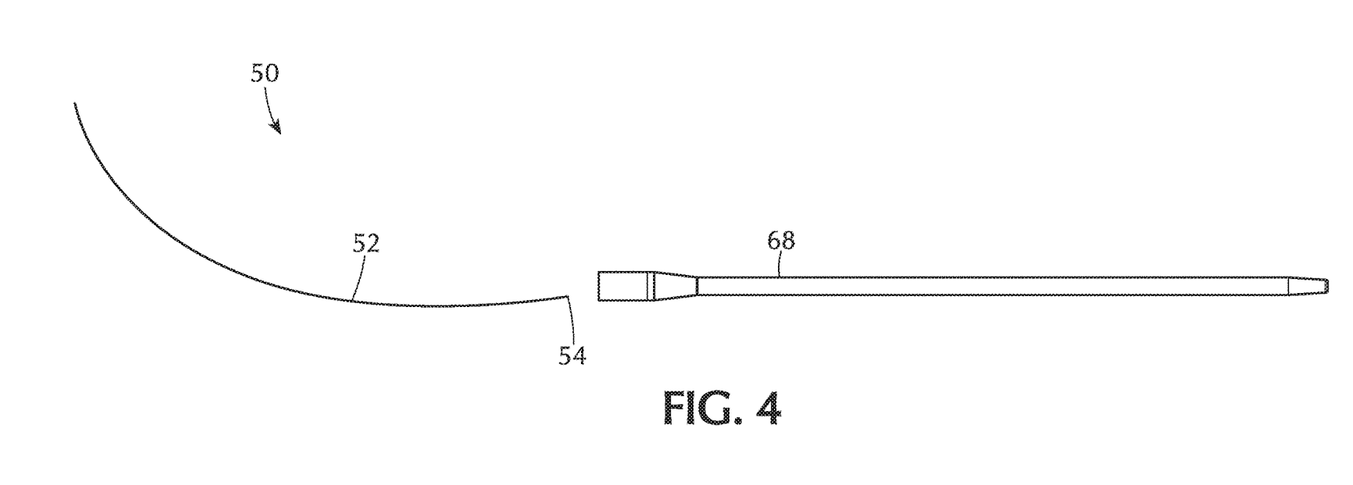
FIG. 4 is a top plan view of a top plan view of an intravenous catheter and an invasive medical device.

Referring now to FIGS. 1-3, an exemplary embodiment of a catheter assembly 10 is shown, including a catheter adapter subassembly 12 and a needle subassembly 14. The catheter adapter subassembly 12 comprises a catheter adapter 16, catheter tubing 18 and a securement element 22, and the needle subassembly 14 further includes a needle 20, connected to a needle hub 24, at a hub distal end 23 and a vent plug 26. In other embodiments not shown, the needle 20 can be retracted into the needle hub 24 after the needle 20 has been used to prevent accidental needle sticks of a patient or a clinician. While the embodiments of invasive medical devices described in this disclosure primarily are directed to needles, it will be understood that the invasive medical device can also be in the form of a catheter introducer or a stylet. As used herein, "stylet" refers to a wire run through a catheter or cannula to render it stiff or to remove debris from its lumen. A "catheter introducer" refers to device used to facilitate insertion of an intravenous catheter. FIG. 4 depicts a catheter introducer 50, which may be in the form of a stylet or guidewire, which is sized and shaped to be inserted into an intravenous catheter 68. The guidewire, stylet or catheter introducer has an elongate shaft 52 and a distal tip 54 that can be inserted into the intravenous catheter 68.

Figure 5:
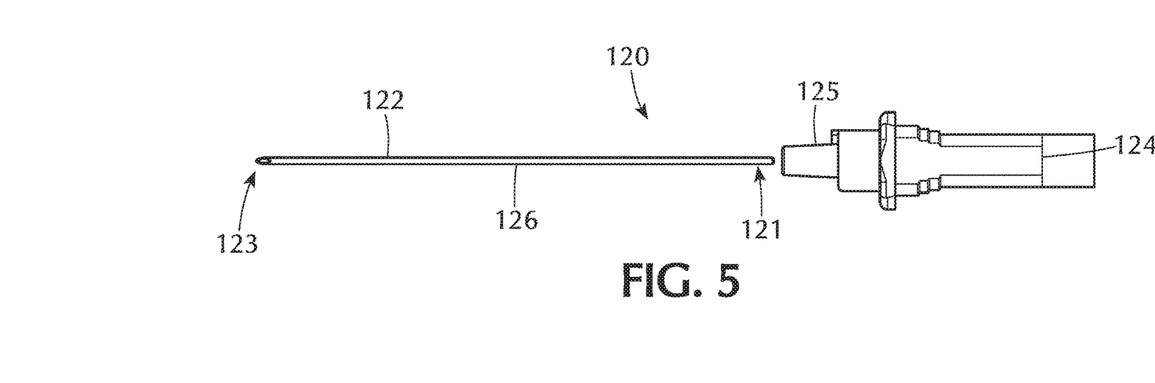
FIG. 5 shows the catheter assembly of with the needle subassembly and catheter adapter subassembly separated.

Referring now to FIG. 5, an embodiment of a needle subassembly 121 is shown including a needle 120 having a cannula 122 defining an elongate shaft 126 having a proximal end 120 and a distal tip 123. The proximal end 120 is connected to a needle hub 124 at hub distal end 125.

Figure 6:
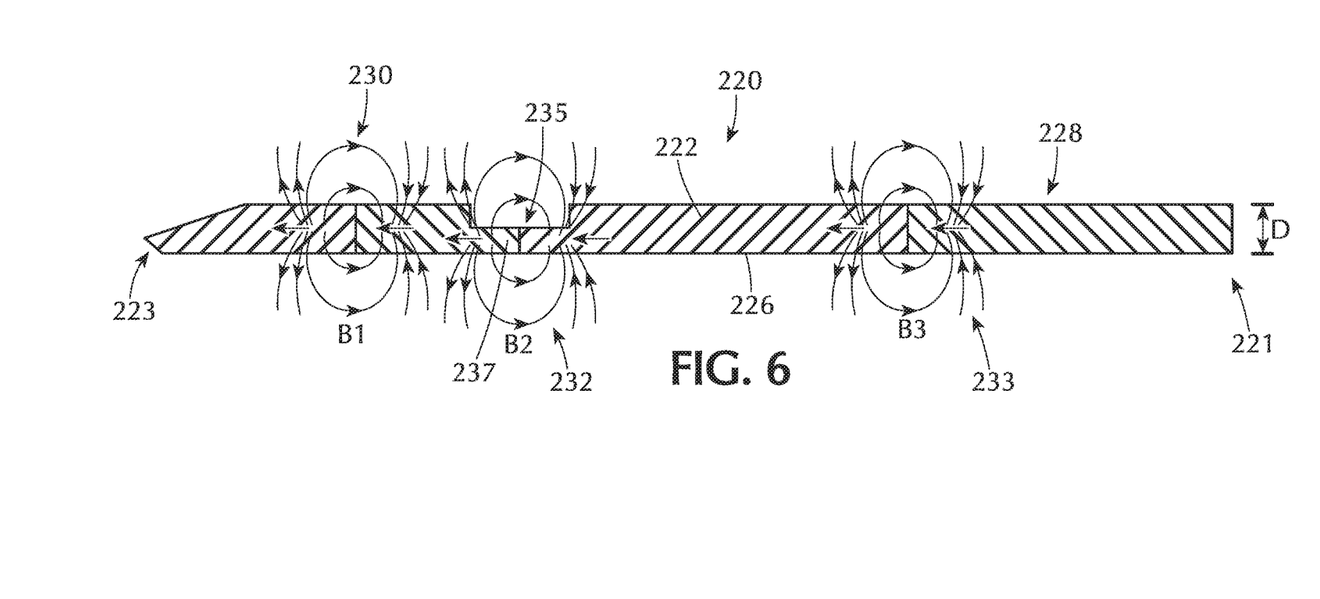
FIG. 6 is a side view of a needle including a notch according an embodiment.

FIG. 6 is enlarged view of a needle a needle 220 having a cannula 222 defining an elongate shaft 226 having a proximal end 221 and a distal tip 223. The needle 220 is sized and shaped for insertion into the vasculature of a patient, which may be through an intravenous catheter. The shaft 226 of the needle 220 defines and outer surface 228 and an outer diameter "D". In the embodiment shown, at least a portion of the elongate shaft 226 includes at least a first magnetic region 230, a second magnetic region 232 and a third magnetic region 233, which are spaced laterally along the shaft 226 of the needle 220. As shown in FIG. 6, the second magnetic region 232 is spaced proximally along the shaft 226 from the first magnetic region 230, and the third magnetic region 233 is spaced proximally along the shaft 226 from the second magnetic region 232. In the embodiment shown, there is a discontinuity 235 in the area of the second magnetic region 232. As shown in FIG. 6, the outer diameter of the needle 220 at the discontinuity 235 is less than the outer diameter "D" at the remainder of the needle 220. It will be understood that that the discontinuity 235 can have an outer diameter that is larger than the outer diameter "D" at the remainder of the needle 220. In either case, the shaft 226 includes an increased or decreased diameter region as a result of the discontinuity 235. In the embodiment shown in FIG. 6, the discontinuity 235 is in the form of a notch 237. The notch 237 is shown as being generally rectangular in shape, however, it will be understood that the notch 237 could be a variety of shapes, including triangular, oval, round, parabolic or irregularly shaped by crimping or other techniques to reduce the diameter at the notch 237. A magnet or magnetic element can be disposed in the notch 237. The first magnetic region 230 has a first magnetic field strength B1, the second magnetic region 232 has a second magnetic field strength B2, and the third magnetic region 233 has a third magnetic field strength B3. In one embodiment, the magnetic field strengths B1, B2 and B3 are equal. In another embodiment each of the magnetic field strengths B1, B2 and B3 are not equal. Magnetic field strength can be measured using a variety of different technologies, including gaussmeters and magnetometers.

According to one or more alternative embodiments, the discontinuity along the shaft of the needle can be in various forms, for example, a layer ferromagnetic metal, a layer of paramagnetic metal, a spot weld of magnetic metal, a ferrule and combinations thereof. According to one or more embodiments, the needle shaft can be slidably disposed within catheter tubing, for example, as shown in FIG. 3, where needle 20 is inserted within catheter tubing 18, as a catheter assembly 10 that includes a catheter adapter subassembly 12 and a needle subassembly 14.

Figure 7:
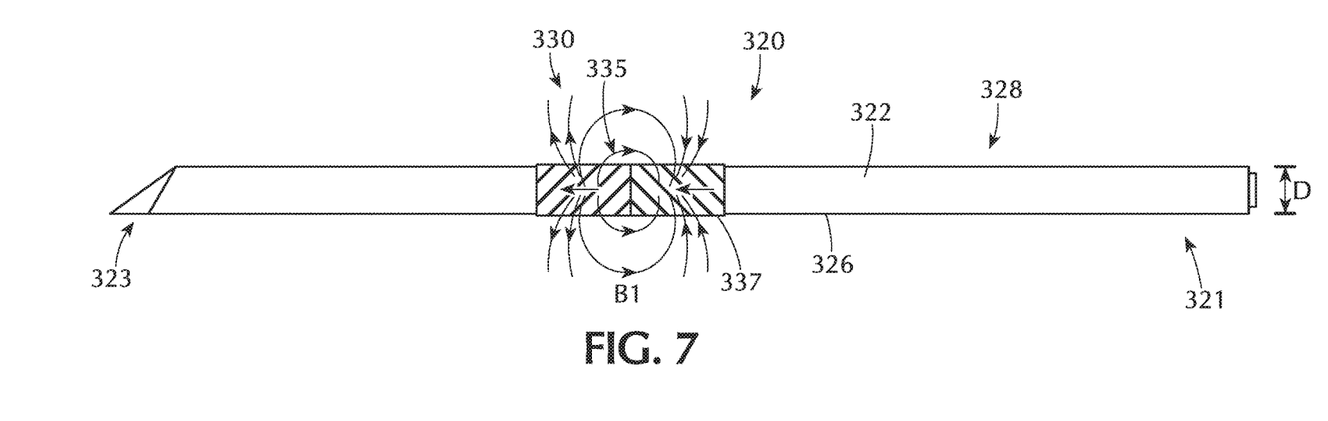
FIG. 7 is a side view of a needle including a magnetic region according an embodiment.

FIG. 7 is enlarged view of a needle a needle 320 having a cannula 322 defining an elongate shaft 326 having a proximal end 321 and a distal tip 323. The needle 320 is sized and shaped for insertion into the vasculature of a patient, which may be through an intravenous catheter. The shaft 326 of the needle 320 defines and outer surface 328 and an outer diameter "D". First magnetic region 330 includes a discontinuity 335, which is provided by a magnetic ferrule 337. The outer diameter of the needle 320 at the discontinuity 335 is greater than the outer diameter "D" at the remainder of the needle 320. The magnetic region 330 has an increased outside diameter at the discontinuity 335 provided by the ferrule.

Figure 8:
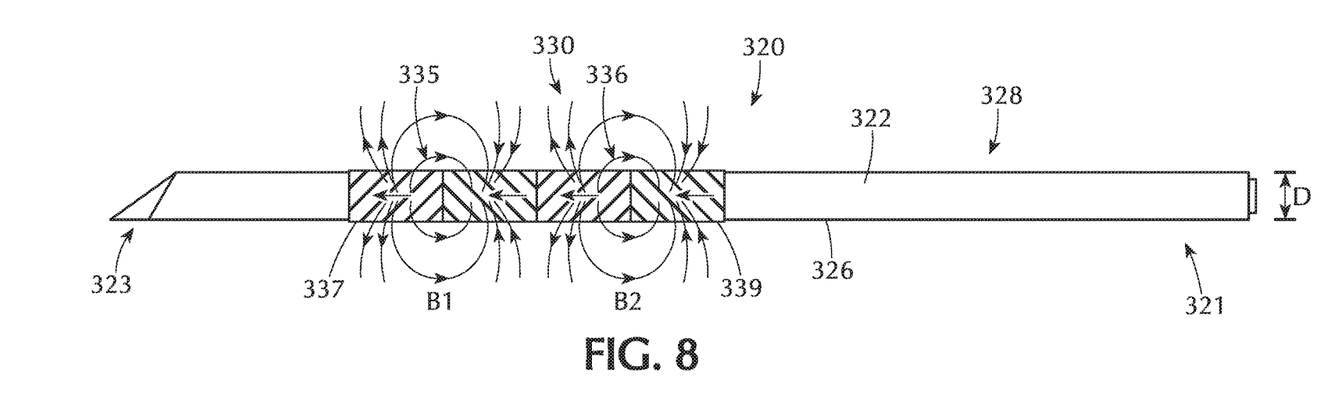
FIG. 8 is a side view of a needle including two magnetic regions according an embodiment.

FIG. 8 shows an embodiment similar to FIG. 7, and further includes a second discontinuity 336 having an outer diameter that is greater than the diameter D of the shaft 326. The second discontinuity is provided by a second ferrule 339.

Figure 9:
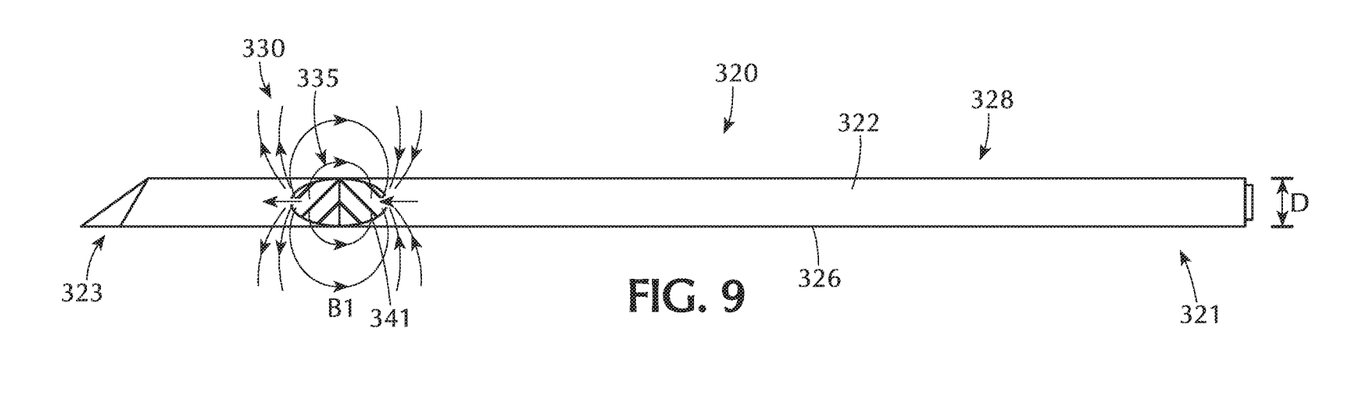
FIG. 9 a side view of a needle including a magnetic adhesive according an embodiment.

FIG. 9 shows an embodiment in which the discontinuity 335 is provided by a magnetic adhesive 341 on the outer surface 328 of the shaft 326, which provides a discontinuity 335 such that the outer diameter at the discontinuity 335 is greater than the outer diameter D of the shaft 326. According to one or more embodiments, the magnetic adhesive includes an additive selected from a paramagnetic additive, a ferromagnetic additive and combinations thereof. The adhesive additive according to one or more embodiments includes a component selected from the group consisting of powdered iron, magnetic iron oxide, magnetic titanium oxide, magnetic powdered steel, and a magnetic iron alloy, and mixtures thereof. In one or more embodiments, the magnetic iron alloy includes one or more of nickel, zinc, and copper. In one or more embodiments, the adhesive additive further comprises a component selected from chromium, magnesium, molybdenum and combinations thereof. The adhesive can be any suitable adhesive such as a curable glue containing magnetizable nanoparticles such as magnetizable metal nanoparticles or magnetizable metal oxide nanoparticles. The magnetizable metal can include iron, cobalt, nickel and alloys of iron, cobalt, and nickel. According to one or more embodiments, the size of the magnetic nanoparticles is in the range of about 1 nanometer (nm) to about 100 nm. In one embodiment, adhesive is a light-curable glue, and in another embodiment, the adhesive is a heat-curable glue.

Figure 10:
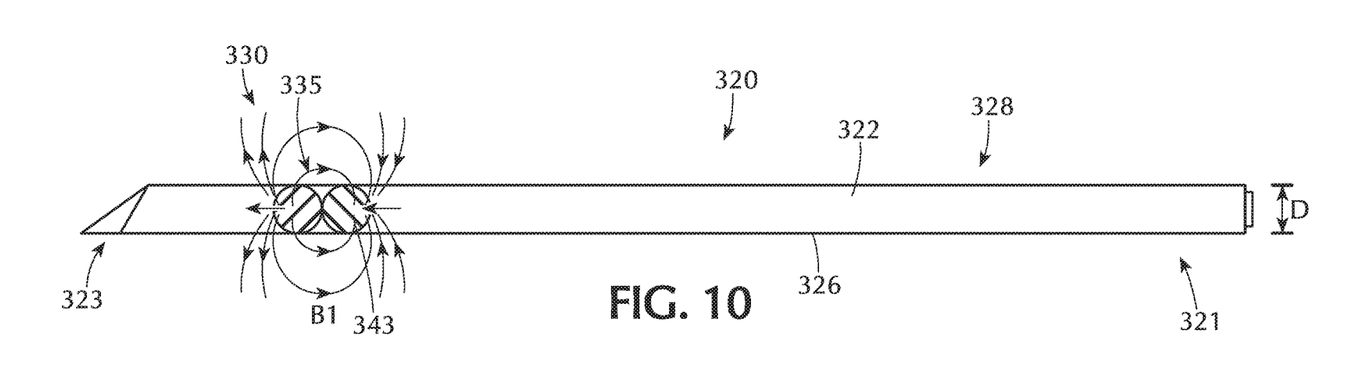
FIG. 10 a side view of a needle a spot weld according an embodiment.

FIG. 10 shows an embodiment in which the discontinuity 335 is provided by a spot weld 343 on the outer surface 328 of the shaft 326, which provides a discontinuity 335 such that the outer diameter at the discontinuity 335 is greater than the outer diameter D of the shaft 326. According to one or more embodiments, the spot weld includes an additive selected from a paramagnetic additive, a ferromagnetic additive and combinations thereof. The spot weld according to one or more embodiments includes a component selected from the group consisting of powdered iron, magnetic iron oxide, magnetic titanium oxide, magnetic powdered steel, and a magnetic iron alloy, and mixtures thereof. In one or more embodiments, the magnetic iron alloy includes one or more of nickel, zinc, and copper. In one or more embodiments, the spot weld additive further comprises a component selected from chromium, magnesium, molybdenum and combinations thereof.

According to one or more embodiments, the shaft has a first magnetic region having a first magnetic field B1 and a second magnetic region having a second magnetic field B2, wherein B1 and B2 are not equal. Alternatively, the first magnetic region has a length L1 and is spaced apart on the shaft at a distance d1 from the second magnetic region which has a length L2 and L1 and L2 are different. In other embodiments, the shaft has a third magnetic region spaced apart at a distance d2 from the first region having a third magnetic field B3 and length L3, wherein B2 and B3 are not equal and L2 and L3 are not equal. According to one or more embodiments, a system is provided in for determining relative position of a needle which includes the needle described according to any of the above described embodiments, and magnetometers positioned with respect to the first magnetic region, the second magnetic region and the third magnetic region.

Figure 11:
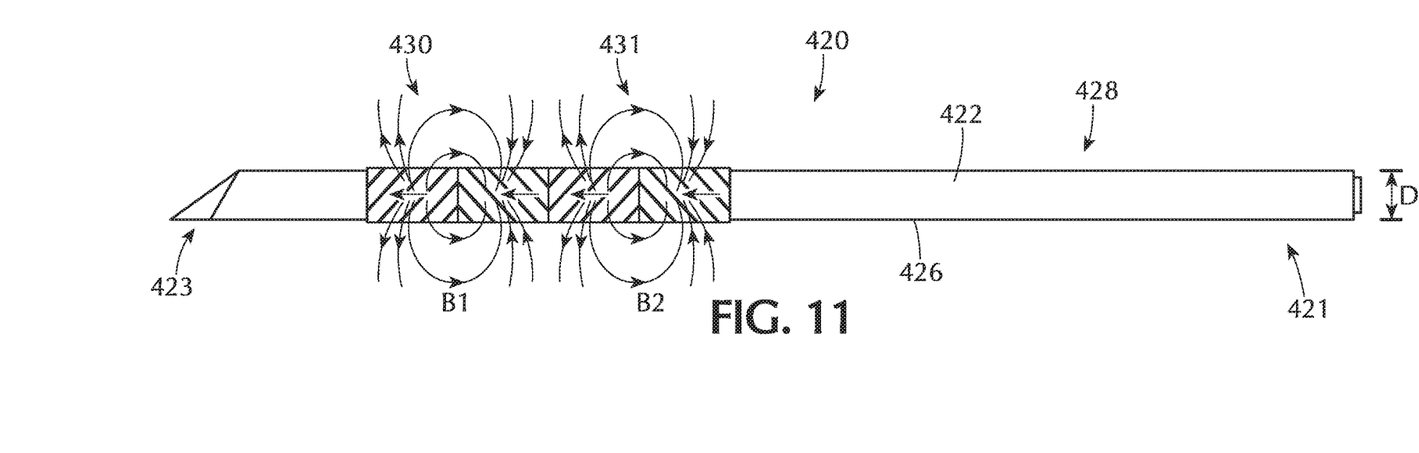
FIG. 11 a side view of a needle including a two magnetic regions according an embodiment.

FIG. 11 shows another embodiment of the disclosure, in which an invasive medical device shown in the form of a needle 420 having a cannula 422 defining an elongate shaft 426 having a proximal end 421 and a distal tip 423. The needle 420 is sized and shaped for insertion into the vasculature of a patient, which may be through an intravenous catheter. The shaft 426 of the needle 420 defines and outer surface 428 and an outer diameter "D". First magnetic region 430 has a first magnetic field strength B1 and second magnetic region 431 has a second magnetic field strength B2. The magnetic regions 430 and 431 can be provided as described above with respect to FIGS. 4-10, or alternatively, the magnetic regions can be provided by cold working the shaft 426 of the needle 420, or modifying the composition of the needle 420 to increase the strength of the magnetic field B1 and B2. In the embodiment shown in FIG. 11, the outer diameter "D" of the shaft 426 may be constant along the length of the needle. Alternatively, there may be a diameter transition at the first magnetic region 430 and/or the second magnetic region 431 such that the outer diameter in the first magnetic region 430 and/or the second magnetic region 431 is larger than the outer diameter of the shaft 426. In other embodiments, there may be a diameter transition at the first magnetic region 430 and/or the second magnetic region 431 such that the outer diameter in the first magnetic region 430 and/or the second magnetic region 431 is smaller than the outer diameter of the shaft 426. The magnetic regions 430 and 431 are shown as being adjacent to each other. In alternative embodiments, the magnetic regions 430 and 431 may be spaced apart. In the embodiment shown, at least one of the magnetic regions 430, 431 is adjacent the distal tip 423.

Figure 12:
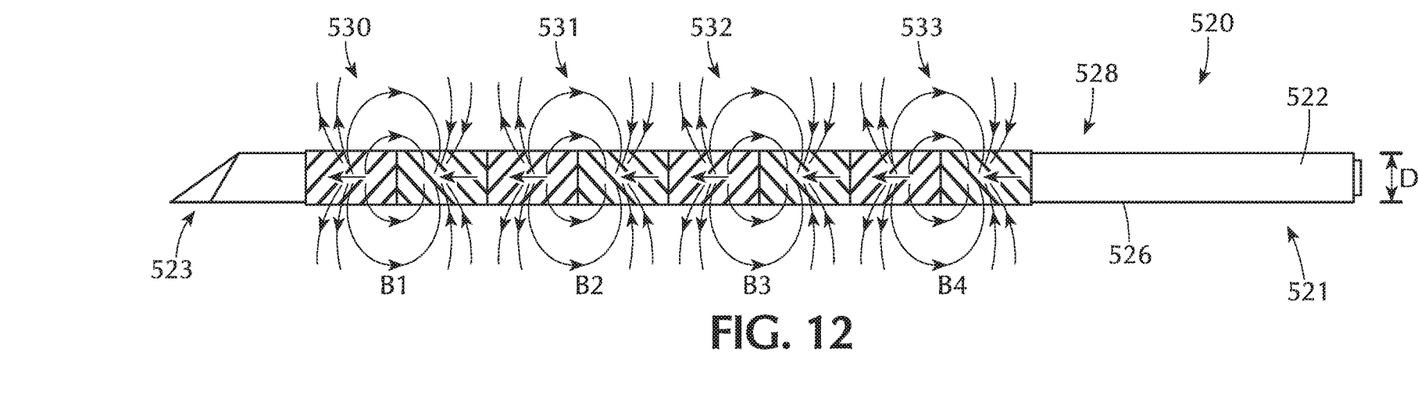
FIG. 12 a side view of a needle including four magnetic regions according an embodiment.

FIG. 12 shows another embodiment in which an invasive medical device shown in the form of a needle 520 having a cannula 522 defining an elongate shaft 526 having a proximal end 521 and a distal tip 523. The needle 520 is sized and shaped for insertion into the vasculature of a patient, which may be through an intravenous catheter. The shaft 526 of the needle 520 defines and outer surface 528 and an outer diameter "D". First magnetic region 530 has a first magnetic field strength B1, second magnetic region 531 has a second magnetic field strength B2, third magnetic region 532 has a third magnetic field strength B3, and fourth magnetic region 533 has a fourth magnetic field strength B4 The magnetic regions 530, 531, 532, and 533 can be provided as described above with respect to FIGS. 4-10, or alternatively, the magnetic regions can be provided by cold working the shaft 526 of the needle 520, or modifying the composition of the needle 520 to increase the strength of the magnetic fields B1, B2, B3, and B4. In the embodiment shown in FIG. 12, the outer diameter "D" of the shaft 526 may be constant along the length of the needle. Alternatively, there may be a diameter transition at the first magnetic region 530 and/or the second magnetic region 531, third magnetic region 532 and fourth magnetic region 533 such that the outer diameter in the first magnetic region 530 and/or the second magnetic region 531, and/or third magnetic region 532 and/or fourth magnetic region 533 is larger than the outer diameter of the shaft 526. In other embodiments, there may be a diameter transition at the first magnetic region 530 and/or the second magnetic region 531, and/or third magnetic region 532, and/or fourth magnetic region 533 such that the outer diameter in the first magnetic region 530 and/or the second magnetic region 531, third magnetic region 532 and/or fourth magnetic region 533 is smaller than the outer diameter of the shaft 526.

It will be understood that while FIG. 12 shows four magnetic regions 531, 532, 533, and 533, the disclosure and claims are not limited to a particular number of magnetic regions. For example, an invasive medical device can have an elongate shaft having one, two, three, four, five, six, seven, eight, nine, ten, or more magnetic regions spaced adjacent to one another or spaced apart along the elongate shaft. As shown in FIG. 11, the second magnetic region 531 is located proximally to the first magnetic region 530, and the third magnetic region 532 is located proximally to the second magnetic region 531 and the fourth magnetic region 533 is located proximally to the third magnetic region 532. In other embodiments, these regions can be proximally spaced.

By providing multiple magnetic regions on the invasive medical device shaft, which can be placed in proximity to the distal tip, a higher degree of precision of device placement guidance can be achieved. In addition, a medical device having a plurality of magnetic regions enables a wide variety and large amount of data to be encoded to or from a magnetic signature on the needle provided by the multiple magnetic regions. Furthermore, invasive medical devices that use only one magnetic marker or region near the tip of the needle, which can have a variety of issues as the single region moves further distances from the sensor as the invasive device is advanced further into the body during a procedure. According to one or more embodiments, a device of the type shown in FIG. 12 having multiple magnetic regions or markers can improve procedural guidance in deep insertions into deeper veins. Multiple magnetic regions proximally adjacent or spaced along the axis of the shaft of the invasive medical device extend the limit of the sensor for deeply inserted device and catheter tips. This allows the sensor (e.g., a magnetometer of an ultrasound system) to continue tracking the magnetic regions located proximally away from the distal end of the medical device, and precisely track the distal tip location for very deep insertions/placements.

Multiple magnetic regions enable the invasive medical device to be encoded with multiple magnetic signatures that will provide procedural guidance systems with greater resolution and precision in locating the needle position. According to one or more embodiments, a system can be provided such that a sensor head can read patterns of magnetic signatures that are written and/or recorded onto the invasive medical device shaft. This technique is analogous to a rotational disk drive used for a computer memory, where patterns of magnetic signatures are recorded onto a magnetic substrate using current from a read/write head, and then the data is read back when required. Thus, according to one or more embodiments, an invasive medical device is provided, for example, a needle, a catheter introducer or a stylet contains a plurality of magnetic regions on the shaft of the invasive medical device, and a read/write head using current records patterns of magnetic signatures to encode information into the invasive medical device. An invasive medical device containing such magnetic signatures encoded onto the device provides a higher level of accuracy when sensing the position of the medical device (e.g., a needle) and can provide information to the sensor head about the device, for example, gauge, outside diameter, size, length, brand, type, etc.

Figure 13:
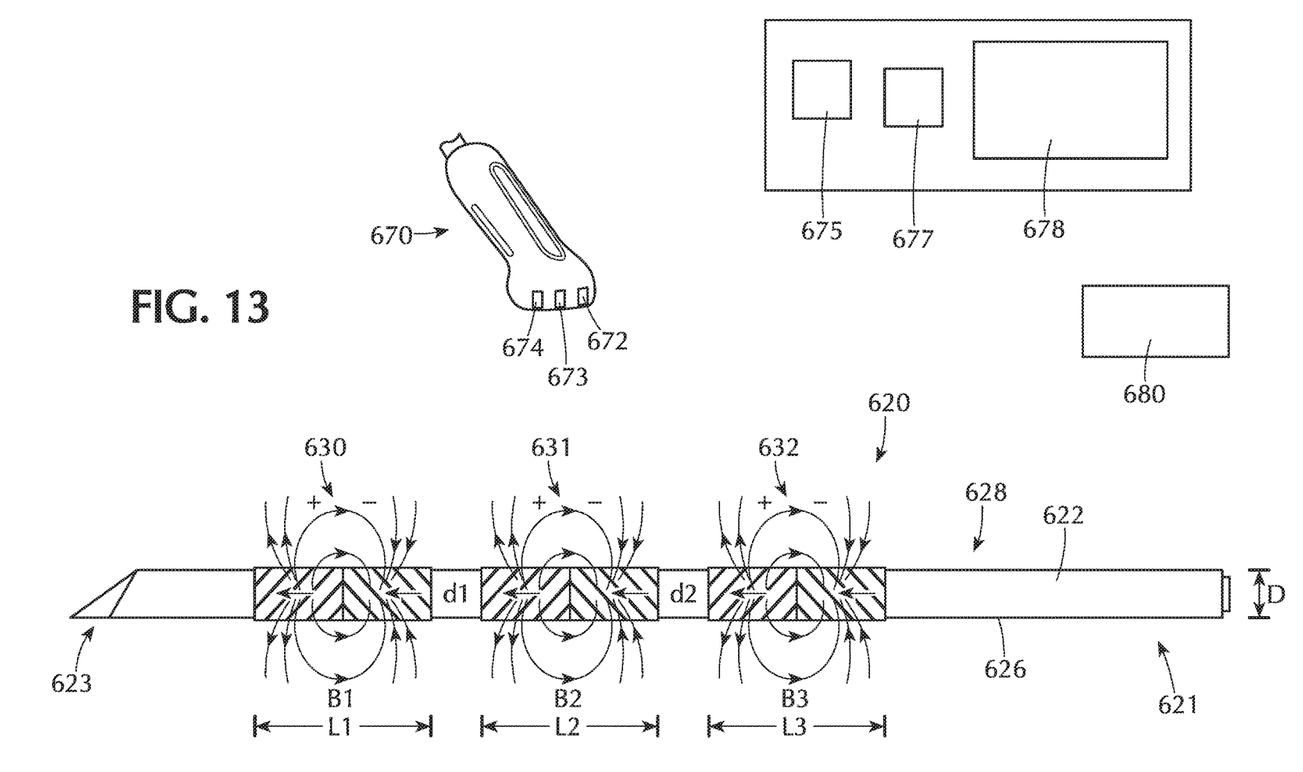
FIG. 13 shows an embodiment of a system including a needle with multiple magnetic regions.

Encoding of information on the shaft of an invasive medical device such as a needle can be accomplished in several ways. FIG. 13 shows another embodiment in which an invasive medical device shown in the form of a needle 620 having a cannula 622 defining an elongate shaft 626 having a proximal end 621 and a distal tip 623. The shaft 626 of the needle 620 defines and outer surface 628 and an outer diameter "D". First magnetic region 630 has a first magnetic field strength B1, second magnetic region 631 has a second magnetic field strength B2, and third magnetic region 632 has a third magnetic field strength B3. The magnetic regions 630, 631, and 632, can be provided as described above with respect to FIGS. 4-12, or alternatively, the magnetic regions can be provided by cold working the shaft 626 of the needle 620, or modifying the composition of the needle 620 to increase the strength of the magnetic fields B1, B2, and B3. In the embodiment shown in FIG. 13, the outer diameter "D" of the shaft 626 may be constant along the length of the needle. Alternatively, there may be a diameter transition at the first magnetic region 630 and/or the second magnetic region 631, and third magnetic region 632 such that the outer diameter in the first magnetic region 630 and/or the second magnetic region 631, and/or third magnetic region 532 is larger than the outer diameter of the shaft 626. According to one or more embodiments, the magnetic regions shown in FIG. 13 are prepared by insulating and coating the shaft with a magnetic layer. Then the shaft of the device can be "written" with a signature indicating the type of device, gauge, geometry of the distal tip, and length by varying the length and/or field strength of the magnetic regions 630, 631, 632. Alternatively a distance d1 and d2 between the magnetic regions 630, 631 and 632 and where the magnetic regions switch polarity can provide the encoding to enable storage of a large amount of information. Furthermore, the length of each magnetic region L1 for magnetic region 630, L2 for magnetic region 631 and L3 for magnetic region 633 can be varied to provide a way of encoding information. Thus, an encoding scheme can be developed that uses one or more features of magnetic regions 630, 631 and 632 to encode information regarding the 620. For example, a combination of the lengths L1, L2 and L3 together with the spacings d1 and d2 can be used to device a code or signature to provide information about the needle 620 such as the needle length, needle gauge, type of needle or other information about the needle 620. Furthermore, each magnetic region 630, 631 and 632 is shown as having a pole orientation of +/− from the distal toward the proximal end. In one or more embodiments, the pole orientations can be varied to provide an additional way to encode needle information. Thus, while magnetic regions 630, 631 and 632 are shown as having pole orientations of +/−, +/− and +/−, these pole orientations can be varied in any number of ways such as +/−, −/+ and +/−, or alternatively, −/+, +/− and −/+. Thus, by changing pole orientation of the magnetic regions, another variable of the magnetic regions can be utilized to provide another way to encode needle information. A detector head 670 containing a plurality of spaced sensors 672, 673 and 674 (for example, magnetometers) can be used to detect magnetic field strength, length and spacing of the magnetic regions. The detector head 670 can be in wired or wireless communication with a processor 675 adapted to determine process data from the information encoded on the shaft of the medical device and/or data pertaining to the detected field the position and orientation of the magnetic regions relative to the detector head 670. This magnetically detected position can then displayed on a display 678 together with the ultrasound image. The processor 675 can be in communication with a memory 677 that stores the encoded information pertaining to the needle 620. The processor can access or look up encoded information stored on the memory to obtain information about the needle.

The detector head 670 can be connected by a wireless connection to a base unit 680 which is in wireless or wired (e.g. USB) communication with the processor 675 and the display 678. The base unit 680 can be integrated with, or some of its functions performed by, the processor 675 or the detector head 670. The base unit 680 receives measurements from detector head 670 and calculates the position, or optionally the position and orientation, of magnetic regions. The base unit 680 can also receive additional information such as the state of charge of the magnetometric detector's battery and information can be sent from the base unit 680 to the detector head 670, such as configuration information. The base unit 680 forwards the results of its calculations, i.e. the position and, optionally, orientation, to the processor 675 for inclusion in the displayed ultrasound image of an image of the invasive device, for example, the needle 620.

It will be appreciated that FIG. 13 is not drawn to scale or density of the encoding, but representative in the fact that the detector head and the encoding can be optimized for the correct amount of signal resolution and information desired to be conveyed.

Thus, FIG. 13 illustrates a system for determining relative position of an invasive medical device such as a needle, as magnetometers positioned with respect to the one or more magnetic regions on the shaft of the medical device. In one or more embodiments, the needle shown in FIG. 13 can be part of a needle subassembly further including a needle hub mounted to the proximal end of the needle, and the needle subassembly can be part of a catheter assembly as shown in FIGS. 1-3, and include intravenous catheter tubing as part of a catheter adapter subassembly. The catheter adapter subassembly can include magnetic feature, such as a magnetizable feature magnetizable by an applied magnetic field or a permanent magnet. The magnetizable feature on the catheter adapter can be a conical metal mandrel for connecting the catheter tubing to the hub catheter or tubing adhesive which can be any suitable adhesive such as a curable glue containing magnetizable nanoparticles such as magnetizable metal nanoparticles or magnetizable metal oxide nanoparticles. The magnetizable metal can include iron, cobalt, nickel and alloys of iron, cobalt, and nickel. According to one or more embodiments, the size of the magnetic nanoparticles is in the range of about 1 nanometer (nm) to about 100 nm. In one embodiment, adhesive is a light-curable glue, and in another embodiment, the adhesive is a heat-curable glue. In other embodiments, a blood control component of the catheter adapter subassembly provides the magnetizable feature. According to one or more embodiments, the blood control component is made from martensitic or ferritic stainless steels, for example, type 420 or type 430 stainless steel. The blood control component (metal spring for instance) or the needle tip safety clip or v-clip that moves with the catheter adapter until fully advanced. In one or more embodiments, the magnetic feature on the catheter adapter subassembly includes a magnetic wedge on the catheter adapter body.

In one or more embodiments, the catheter adapter subassembly includes the magnetizable feature, wherein the magnetizable feature includes magnetizable catheter tubing. In one or more embodiments, at least a portion of the polyurethane tubing comprises a magnetizable composition which is magnetizable by an externally applied magnetic field, the magnetizable composition comprising a magnetic material dispersed in the polyurethane. In certain embodiments, the magnetic composition is dispersed in the polymeric material, for example, polyurethane, which forms the tubing. In a specific embodiment, the magnetizable composition comprises an inner layer surrounding the lumen of the catheter with an outer layer of non-magnetizable polymeric material, for example, polyurethane. In an alternative specific embodiment, the layer of magnetizable composition is an outer layer surrounding an inner layer of non-magnetizable polyurethane. In one or more embodiments, the magnetizable composition forms longitudinal segments of the catheter separated by longitudinal segments of non-magnetizable polymeric material, for example, polyurethane.

In any of the foregoing embodiments of the catheter, the magnetizable composition may further comprise a radiopaque component. Alternatively, in any of the foregoing embodiments, a non-magnetizable portion of catheter may comprise a radiopaque component.

The magnetometers of the system can include three different magnetometers arranged in a three-dimensional grid array as part of an ultrasound system which can derive a three-dimensional correlation to obtain a distance from the grid array to at least one of the first magnetic field, the second magnetic field and the third magnetic field. In one or more embodiments, the three-dimensional correlation is determined by a function $I=f(B_i,\mu_r)$, where $i=x$ or y or z along three axes, x, y and z are distances in three planes, and B is a known magnetic field produced by the first magnetic field, the second magnetic field and the third magnetic field. A system including a magnetic feature on the catheter adapter subassembly and the needle subassembly can be used to determine relative motion of the needle and the catheter adapter subassembly as the needle is disposed within intravenous catheter tubing and they are slidably moved with respect to each other.

Another aspect of the disclosure pertains to a method obtaining information about an invasive medical device, which includes encoding magnetic data on an invasive medical device with a plurality of magnetic fields, the medical device selected a guidewire, a catheter introducer, a stylet and a hypodermic needle; and reading the data encoded on the invasive medical device. The reading can be accomplished as described above, using an ultrasound head with a plurality of magnetometers. The data can include at least one of the diameter of the medical device, the length of the medical device and the type of the medical device. In one or more embodiments, a method can include encoding the shaft of an invasive medical device such as a catheter introducer, a stylet and a needle, and encoding is accomplished by correlating information with respect to length and/or spacing of a plurality of magnetic fields adjacent to each other or spaced apart on the shaft of the medical device. In one or more embodiments, reading data from the medical device includes reading a position of the magnetic fields with respect to the distal tip of the needle. Reading the data in one or more embodiments utilizes a three-dimensional array of magnetometers as part of an ultrasound system, and the ultrasound system derives a three-dimensional correlation to obtain a distance from the array of magnetometers to at least one of the magnetic fields. In one or more embodiments of the method, the three-dimensional correlation is determined by the function $I=f(B_i, \mu_r)$, where $i=x$ or y or z along three axes, x, y, and z, which are distances in three planes, and B is a known magnetic field produced by at least one of the magnetic fields.

A second way of encoding the shaft of an invasive medical device would be to replicate the magnetic feature (ferrule, drop of magnetic adhesive, spot weld, etc. at intervals along the shaft. The distance between the magnetic regions could be encoded to give the type, gauge and length of the product used, In addition, the plurality of magnetic regions can be used for visualization of the device during an insertion procedure.

The magnetic regions according to any of the embodiments described above can be provided in a variety of ways, in addition to those specifically discussed. A common material used to make invasive medical devices such as needles, stylets and introducers includes stainless steel, namely type 304 or type 316 stainless steel. There are five classes of stainless steel, namely, ferritic (e.g., types 405, 430, 442), austenitic (e.g., types 201, 301, 302, 303, 304, 316), martensitic (e.g., types 403, 410, 416), duplex (e.g., types 2205, Alloy 255), and precipitate-hardened (e.g., types 17-4PH, PH 17-7) and generally, only austenitic stainless steel is nonmagnetic. The first four classes are defined based on the microstructure of the metal with the last class, precipitate-hardened, based on its heat treatment. Microstructure provides the stainless steel its magnetic properties.

However, while austenitic stainless steel is not magnetic, it can be magnetic by modifying the material in a number of ways. For example, a portion of the microstructure can be changed to any one of the other four classes listed above so that the material would have some magnetic permeability, i.e. magnetism, built into the material. The microstructure of austenitic stainless steel can be changed by a process called martensitic stress induced transformation. This is a microstructural change from austenite to martensite, and the transformation can occur due to cold working as well as slow cooling from austenitizing temperatures. After cold working or slow cooling an austenitic stainless steel will have an appreciable level of martensitic microstructure. Due to martensite being magnetic, the once nonmagnetic austenitic stainless steel will now have a degree of magnetism.

Low alloy content stainless steel (particularly that of low nickel, carbon, and/or nitrogen) are more susceptible to martensitic stress induced transformation than stainless steel with higher alloying elements. Type 304 is an example of a stainless steel that is quite susceptible to forming martensite after cold working.

The austenite in the alloy transforms into martensite at high degrees of cold working relative to the tempered state. Typically the susceptibility could increase from ~100 ppm to 10,000 ppm when annealed stainless steel is cold worked to full hardness. To increase the susceptibility, additional cold working of the needle shaft to induce a higher amount of martensite in the alloy, needles may be spring tempered to maximize the mechanical properties after cold working. Additionally the needle may be heat-treated to remove excess martensite and control the exact amount of desired susceptibility.

According to one or more embodiments, to increase the magnetization of the material used to make the invasive medical device, the alloy composition of the needle could be enhanced by adding ferromagnetic metal to the alloy. For example, type 304 stainless steel typically contains 18% Cr by weight and 8% Ni by weight with a max of 2% Mn by weight. In an embodiment, to provide a stainless steel with higher magnetic susceptibility, cobalt could be added to this alloy in quantities ranging from 0.01% to 5% by weight, and/or the manganese content could be increased from the maximum allowable 2% to 3%, 4% or 5% by weight. Additionally, rare-earth metals such as gadolinium or neodymium could be added in small quantities <5% by weight to further enhance magnetic susceptibility of the alloy. Any of these materials can be used in the region of the discontinuity described above, whether by adding a layer of material, a ferrule, a crimp or a spot weld.

In one or more embodiments, magnetic susceptibility could also be enhanced by adding layers of a ferromagnetic metal to the shaft of the invasive medical device. In an exemplary embodiment, a needle having an outer diameter of approximately 0.5-1.5 mm can also have a plating of nickel deposited by electroplating or electroless plating methods in thicknesses ranging from 0.1 microns to 100 microns to increase magnetic susceptibility of the magnetic region or regions. In alternative embodiments, layers of other metals could be applied to improve specific properties, such as a layer of Cr or $CrO_2$ on the outside to prevent corrosion, or an intermediate layer of Co or Neodymium to increase magnetic susceptibility.

Other examples include adding a coaxial layer of a ferromagnetic material such as iron within the tubing used to make the needle. Additional surface barriers layers can be applied by electroplating or other suitable techniques to machined or ground surfaces where a potentially toxic metal like Co or Fe would be otherwise exposed.

Magnetic tip location sensing can also be improved according to one or more embodiments by placing a magnetic region closer to one end of the needle, preferably the sharp distal tip of the needle. If the magnetic region is placed at a known location at a fixed distance from the tip of the needle, then arrays of magnetometers as can be used to measure the magnetic field strength variation from the magnetic region and locate the distal tip of the needle. According to one or more embodiments that include a ferrule, the ferrule may also serve other functions such as needle stick injury prevention. The ferrule may be made of a material of higher or lower magnetic susceptibility than the rest of the needle and may be attached by spot welding to the needle. Alternatively, a spot weld of material may be deposited over the needle surface by welding it on and such a spot may also serve a another function in a needle stick injury prevention feature.

In embodiments that include magnetic adhesive, according to one or more embodiments, the adhesive is applied to the needle shaft, and is located under the catheter when the needle is inserted into the catheter tubing, and thus the patient will not perceive or sense the presence of the adhesive. According to one or more embodiments, the magnetic adhesive provide the magnetic region on the device to enable detection of the needle and provide guidance the visualization system requires, and the adhesive could also be used prevent the needle from passing through a safety washer in systems that include safety washer.

Another aspect of the disclosure pertains to a system for determining catheter tip location when the catheter tubing is inserted in a patient. According to one or more embodiments, a system provides a way to independently measure the cannula tubing tip location by measuring the location and vector of the permanent magnet, and calculating and predicting the catheter tip location relative to the position of the magnetic sensor(s) on an ultrasound probe and the ultrasound information transmitted from the sensors on the ultrasound probe. A permanent magnet on a device with north and south poles on axis with the catheter and needle and a known geometrical relationship to one or more features fixed on the catheter assembly provides a measurement datum that is measureable by the ultrasound probe magnetic sensors. From the measurement datum based on the one or more features on the catheter assembly, the direction vector and position of the catheter tip or other features can be calculated. A magnetized magnetizable needle or feature on the needle can then be used to independently measure the position of the needle tip. The measured position of the needle tip or feature on the needle can then be compared relative to the calculated position of the catheter tip to provide more specific information related to the catheter placement process, such as needle and catheter tip position relative to the patient's anatomy. This information can be used to determine (a) if the catheter is properly seated and ready for insertion (i.e., no over the bevel condition), (b) when the needle tip is in the "hooded" position (needle tip just inside of the catheter tip), and (c) and (d) when the catheter is advanced to specific distances and at angles suggesting successful placement in the vein.

Figure 14:
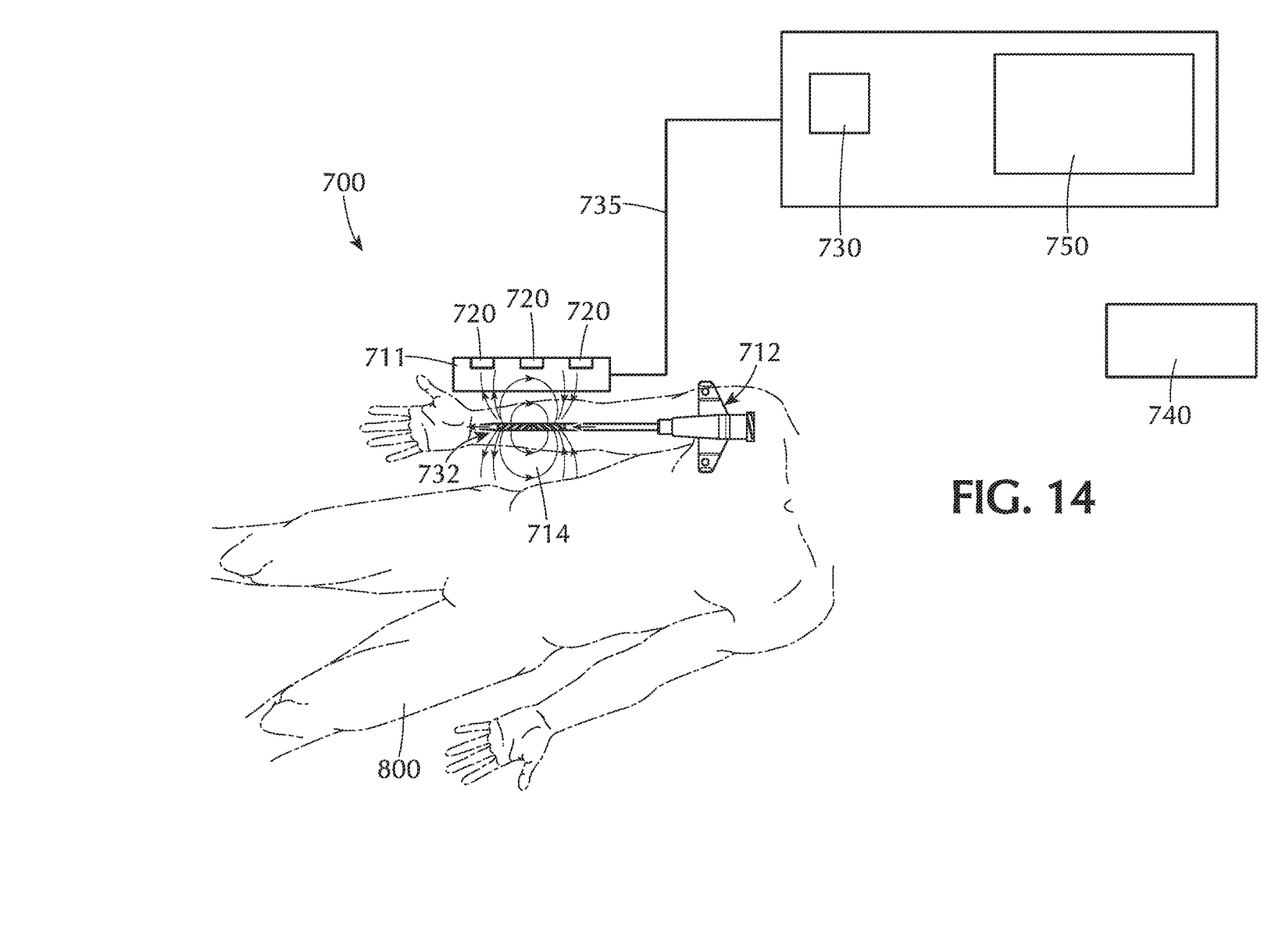
FIG. 14 shows an embodiment of a system including a catheter assembly and a needle according to an embodiment.

FIG. 14 shows an ultrasound system 700 including a catheter adapter subassembly 712 comprising a magnetizable feature 732 that has been magnetized as described herein is shown inside of a patient's body 800. A magnetometric detector 711 comprising an array of magnetometers 720 (which can be housed in a probe of an ultrasound system, not shown) arranged in a 3-D array can be used to sense the magnetic field 714 together with the terrestrial magnetic field and any other background magnetic field. The magnetometric detector 711 is in communication with an ultrasound processor 730 adapted to determine from the detected field the position and orientation of the magnetizable feature 732 relative to the magnetometric detector 711. This magnetically detected position is then displayed on a display 750 together with the ultrasound image.

The ultrasound system 700 can be a two dimensional B-mode ultrasound system with an ultrasound probe modified by the provision of the magnetometric detector 711. The ultrasound processor 730, which can be connected to the ultrasound probe via a cable 735, sends electrical signals to the magnetometric detector 711 to cause it to generate ultrasound pulses and interpreting the raw data received from the transducer probe housing the magnetometric detector 711, which represents echoes from the patient's body, to assemble it into an image of the patient's tissue.

The magnetometric detector 711 can be attached to the ultrasound probe and can be battery powered or powered from the ultrasound system. In specific embodiments, positioning elements are provided on the magnetometric detector 711 to ensure that it is always attached in the same well-defined position and orientation. The magnetometric detector 711 can connected by a wireless connection to a base unit 740 which is in wireless or wired (e.g. USB) communication with the ultrasound processor 730 and the display 750. The base unit 740 can be integrated with, or some of its functions performed by, the ultrasound processor 730 or the magnetometric detector 711.

The base unit 740 receives normalized measurements from magnetometric detector 711 and calculates the position, or optionally the position and orientation, of magnetizable feature 732. The base unit 740 can also receive additional information such as the state of charge of the magnetometric detector's battery and information can be sent from the base unit 740 to the magnetometric detector 711, such as configuration information. The base unit 740 forwards the results of its calculations, i.e. the position and, optionally, orientation, to the ultrasound processor 730 for inclusion in the displayed ultrasound image of an image of the catheter.

In one or more embodiments, the base unit 740 can be integrated into the ultrasound system 700 with the ultrasound processor 730 and the magnetometric detector 711 being in direct communication with the ultrasound system 700 either via wireless link or using the same physical cable 735.

Thus, in one or more embodiments, the magnetizable feature is magnetized using any suitable device that can produce a magnetic field to magnetize a needle or medical device to produce a magnetic field B at a distance x through tissue of permeability $\mu_r$, and the correlation is calculated as $x=f(B, \mu_r)$. In one or more embodiments, three magnetometers 720 are placed orthogonally to each other and used to derive a 3-dimensional correlation $I=f(B_i, \mu_r)$, wherein $i=x$ or y or z along three axes. In a specific embodiment, the distance from the magnetizable feature to the 3-dimensional array of magnetometers is calculated. In a further specific embodiment, location of the array of magnetometers in reference to an ultrasound sensor of an ultrasound imaging system is used to calculate a location of the magnetizable feature with respect to the ultrasound sensor. In another specific embodiment, the method comprises displaying an image of the magnetizable feature.

Although the disclosure herein provided a description with reference to particular embodiments, it is to be understood that these embodiments are merely illustrative of the principles and applications of the disclosure. It will be apparent to those skilled in the art that various modifications and variations can be made to the devices, methods and systems described in the present disclosure without departing from the spirit and scope thereof. Thus, it is intended that the present disclosure include modifications and variations that are within the scope of the appended claims and their equivalents.

What is claimed is:

1. An invasive medical device for insertion into a patient, the invasive medical device comprising:
a hypodermic needle comprising a stainless steel elongate shaft having a diameter, an outer surface, a distal tip, and a proximal end, the diameter of the elongate shaft sized to be inserted within an intravenous catheter, at least a portion of the elongate shaft having a first magnetic region comprising a first magnetic field B1 having a known magnetic field strength, a vector, and a first length L1, and placed at a known location at first fixed distance from the distal tip and spaced apart at a distance d1 from a second magnetic region comprising a second magnetic field B2 having a known magnetic field strength, a vector, and a second length L2, and placed at a known location at second fixed distance from the distal tip, and a third magnetic region spaced from the second magnetic region at a distance d2 and comprising a third magnetic field B3 having a known magnetic field strength, a vector, and a third length L3, wherein L1 and L2 are not equal, wherein L2 and L3 are not equal, and wherein L1, L2 and L3, and d1 and d2 are utilized to encode the hypodermic needle with information on the elongate shaft, wherein the first magnetic region and the second magnetic region are separated by a non-magnetized region and wherein the second magnetic region and the third magnetic region are separated by a non-magnetized region, wherein the first magnetic region, the second magnetic region and the third magnetic region alternate in pole orientation to encode the hypodermic needle with information on the elongate shaft, wherein the information includes one or more of diameter, length and type of device.

2. The invasive medical device of claim 1, wherein at least one of the first magnetic region and the second magnetic region is selected from the group consisting of a layer of ferromagnetic metal, a layer of paramagnetic metal, a notch in the outer surface of the elongate shaft, a spot weld of magnetic metal, a ferrule and combinations thereof.

3. A system comprising the invasive medical device of claim 1 and further comprising an ultrasound system comprising a three-dimensional grid array of magnetometers, wherein the ultrasound system is configured to determine a position of the first magnetic region, the second magnetic region and the third magnetic region of the hypodermic needle.

4. The invasive medical device of claim 1, wherein at least one of the first magnetic region, the second magnetic region and the third magnetic region comprises martensitic steel.

5. An invasive medical device for insertion into a patient, the invasive medical device comprising:
a hypodermic needle comprising a stainless steel elongate shaft having a diameter, an outer surface, a distal tip, and a proximal end, the diameter of the elongate shaft sized to be inserted within an intravenous catheter, at least a portion of the elongate shaft having a first magnetic region comprising a first magnetic field B1 having a known magnetic field strength, a vector, and a first length L1, and placed at a known location at first fixed distance from the distal tip and spaced apart at a distance d1 from a second magnetic region comprising a second magnetic field B2 having a known magnetic field strength, a vector, and a second length L2, and placed at a known location at second fixed distance from the distal tip, and a third magnetic region spaced from the second magnetic region at a distance d2 and comprising a third magnetic field B3 having a known magnetic field strength, a vector, and a third length L3, wherein the first magnetic region is adjacent the distal tip and B1 and B2 are not equal and L1 and L2 are not equal, wherein L2 and L3 are not equal, and wherein L1, L2 and L3, and d1 and d2 are utilized to encode the hypodermic needle with information on the elongate shaft, wherein the first magnetic region and the second magnetic region are separated by a non-magnetized region and wherein the second magnetic region and the third magnetic region are separated by a non-magnetized region, wherein the first magnetic region, the second magnetic region and the third magnetic region alternate in pole orientation to encode the hypodermic needle with information on the elongate shaft, wherein the information includes one or more of diameter, length and type of device.

6. The invasive medical device of claim 5, wherein the second magnetic region is spaced proximally from the first magnetic region.

7. The invasive medical device of claim 6, wherein each of the first magnetic region, the second magnetic region and the third magnetic region comprise at least one of a layer of ferromagnetic metal, a layer of paramagnetic metal, a spot weld of magnetic metal, a ferrule and combinations thereof.

8. The invasive medical device of claim 5, wherein each of the first magnetic region and the second magnetic region comprise at least one of a layer of ferromagnetic metal, a layer of paramagnetic metal, a spot weld of magnetic metal, a ferrule and combinations thereof.

9. A system comprising the invasive medical device of claim 7 and an ultrasound system including a three-dimensional grid array of magnetometers, wherein the ultrasound system for determining relative position of the hypodermic needle is configured to determine an x, y, or z position of the first magnetic region and the second magnetic region.

10. The system of claim 9, wherein the hypodermic needle is part of a needle subassembly further including a needle hub mounted to the proximal end of the hypodermic needle, and the intravenous catheter is part of a catheter adapter subassembly, the catheter adapter subassembly including a magnetic feature.

11. The system of claim 10, wherein the ultrasound system is configured to detect the known magnetic field strength, vector, length and spacing of the first magnetic region from the second magnetic region and the third magnetic region.

12. The system of claim 11, wherein the ultrasound system calculates the position of the hypodermic needle.

13. The system of claim 11, wherein the ultrasound system is configured to determine relative motion of the hypodermic needle and the catheter adapter subassembly.

* * * * *